US009974976B2

(12) United States Patent
Frigo

(10) Patent No.: US 9,974,976 B2
(45) Date of Patent: May 22, 2018

(54) TISSUE COMPENSATOR THICKNESS VISUALIZATION AND MODIFICATION TOOL FOR USE IN RADIATION TREATMENT PLANNING

(71) Applicant: KONINKLIJKE PHILIPS N.V., Eindhoven (NL)

(72) Inventor: Sean Frigo, Marshall, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 295 days.

(21) Appl. No.: 14/787,785

(22) PCT Filed: May 15, 2014

(86) PCT No.: PCT/IB2014/061446
§ 371 (c)(1),
(2) Date: Oct. 29, 2015

(87) PCT Pub. No.: WO2014/188308
PCT Pub. Date: Nov. 27, 2014

(65) Prior Publication Data
US 2016/0082289 A1    Mar. 24, 2016

Related U.S. Application Data

(60) Provisional application No. 61/826,171, filed on May 22, 2013.

(51) Int. Cl.
*A61N 5/10* (2006.01)
(52) U.S. Cl.
CPC ........... *A61N 5/1039* (2013.01); *A61N 5/103* (2013.01); *A61N 5/1031* (2013.01);
(Continued)

(58) Field of Classification Search
CPC ........... A61N 5/103; A61N 2005/1087; A61N 2005/1096; A61N 5/1031; A61N 5/1039; A61N 2005/1074
See application file for complete search history.

(56) References Cited

U.S. PATENT DOCUMENTS

| 6,898,263 B2 | 5/2005 | Avinash et al. |
| 2012/0097871 A1 | 4/2012 | Guertin et al. |
| 2012/0157746 A1* | 6/2012 | Meltsner ................ A61N 5/103 600/1 |

FOREIGN PATENT DOCUMENTS

| WO | 9114397 A1 | 10/1991 |
| WO | WO0009114397 A1 * | 10/1991 |
| WO | 9520354 A1 | 8/1995 |

* cited by examiner

*Primary Examiner* — Christine H Matthews
*Assistant Examiner* — Joshua D Lannu

(57) ABSTRACT

A system for visualizing and modifying the thickness of a compensator for radiation therapy in the context of a desired target and dose coverage thereof includes planar slice image generation module, a visualization unit and an adjustment module. The planar slice image generation module generates a series of planar slice images from a patient image data set disposed with one axis parallel to a radiation beam and one axis perpendicular to the radiation beam. The visualization unit graphically depicts a compensator thickness profile, a target of interest, and/or a dose representation on at least one of the series of planar slice images all in the same plane lying in a beam's longitudinal direction. The adjustment module receives user input of an adjustment of at least one compensator thickness value via a manipulation of the graphical depiction thereof.

18 Claims, 6 Drawing Sheets

(52) U.S. Cl.
CPC ............... *A61N 2005/1074* (2013.01); *A61N 2005/1087* (2013.01); *A61N 2005/1096* (2013.01)

TISSUE COMPENSATOR THICKNESS VISUALIZATION AND MODIFICATION TOOL FOR USE IN RADIATION TREATMENT PLANNING

CROSS REFERENCE TO RELATED APPLICATIONS

This application is a national filing of PCT application Ser. No. PCT/IB2014/061446, filed May 15, 2014, published as WO 2014/188308 A1 on Nov. 27, 2014, which claims the benefit of U.S. provisional application Ser. No. 61/826,171 filed May 22, 2013, which is incorporated herein by reference.

The following relates generally to radiation therapy planning and evaluation. It finds particular application in conjunction with visualizing and specifying the thickness of a compensator to be used in Intensity Modulated Proton Therapy (IMPT) using modulated pencil beams or in constant intensity Broadbeam proton therapy, and will be described with particular reference thereto. The following also relates to visualizing and specifying the thickness of compensator modifiers utilized in Intensity Modulated Radiation Therapy (IMRT). However, it will be understood that it also finds application in other usage scenarios and is not necessarily limited to the aforementioned application. The following description will be in the context of compensator modification and dose assessment for a single beam within a group of beams comprising a treatment plan. It need not however, be restricted to being done only on a per-beam basis, whereby, e.g. the dose depicted and assessed can be dose summed from a number of sources.

A goal of radiation therapy is to deliver lethal doses of radiation to a target region of interest, such as a tumor, while minimizing radiation to other areas, especially organs at risk. Various approaches may be used to deliver radiation during therapy, e.g., IMRT, VMAT, or the like. These approaches deliver radiation doses with well-defined and precisely calculated beams of external radiation to the target region of interest.

In proton radiation therapy, a solid element may be placed in the radiation beam to modify the radiation beam in such a way as to tailor it to a specific patient's anatomy and to create a desired deposition pattern of radiation within the patient. One class of these devices is an aperture or block collimator, which is custom fabricated to define a cross-section of the beam, allowing adjustment of beam edge location in directions lateral to the beam axis and general propagation direction. Another device is called a bolus or a tissue compensator or simply a compensator. Proton beam compensators allow adjustment of proton beam edge locations in directions longitudinal to the beam axis and general propagation direction.

Compensators are used with proton beams and the like to modify the radiation's depth of penetration, or stopping location. By creating a two-dimensional thickness pattern in the solid material comprising the compensator, the stopping depths for all points across the beam's cross section may be adjusted. This is done to create a distal dose surface that can be wrapped around the most downstream surface of the target to be treated.

Often system-calculated thickness compensator values are modified to adjust the depth pattern of radiation dose deposition. The technician planning a radiation therapy treatment for a given patient wants to quickly make these modifications in the thickness pattern of the compensator and simultaneously visualize the resulting dose patterns relative to a patient's anatomy. The visualization should be in a readily interpretable way so the technician can easily assess modifications and their results, while navigating through the patient anatomy.

In order to make adjustments, individual compensator thickness values need to be modified. The most basic and direct method to do so by the technician is via the manual editing of thickness values stored in a table. This is a tedious undertaking and provides no spatial perspective to the effects of the editing. A visualization of this process is needed.

A common approach is to create a visualization in terms of what is called a beam relative view (BRV). This is the perspective as if a person were looking along a treatment beam's central axis into the patient. In this orientation, a plane (slice) orthogonal to the beam axis at a desired depth in the patient's anatomy is displayed along with the compensator's thickness map overlaid. This slice through the 3-D anatomical planning image displays patient anatomy and has superimposed on its segmentations of the target and other organs, isodose lines, and optionally other information. The plane is often at an oblique angle to the three cardinal cut planes (transverse, sagittal, and coronal) in the patient's anatomy.

However, a problem exists with the beam relative view display in that all elements are shown in one plane on top of each other. This makes it difficult to easily determine the individual elements, especially if all are shown simultaneously.

Another problem with the beam relative view is that the technician cannot see the entire distal surface or a continuous contour of the target. Instead, the technician only sees irregular outline contours representing segments of a target's contours present in the visualization slice. These representations often are not regularly connected from slice to slice in a familiar manner, and are therefore difficult to interpret.

Furthermore, current implementations do not allow the technician to see correlations in compensator thickness and isodose levels with the target. This is because the dose levels of interest may be lying in proximal or distal planes to the current slice being visualized showing the target. That is, the technician does not have a clear idea of which plane in which the isodose line lies, or which way to bring the line to the desired location.

The following discloses a new and improved method for visualizing and monitoring compensator thickness which addresses the above-referenced issues, and others.

In accordance with one aspect, a compensator thickness visualization and modification system includes a planar slice image generation module for generating a series of planar slice images from a patient image data set disposed with one view axis parallel to a radiation beam (beam relative view or BRV) and one view axis perpendicular to the radiation beam (perpendicular beam relative view or PBRV). The system also includes a visualization unit for graphically depicting at least one of a compensator thickness profile, a target of interest, and a dose representation on at least one of the series of planar slice images. In addition, the system includes an adjustment module for receiving user input of an adjustment of at least one compensator thickness value via a manipulation of the graphical depiction thereof.

In accordance with another aspect, a method for visualizing and modifying compensator thickness includes generating a plurality of planar reconstructions through a patient image data set. The method further includes graphically depicting at least one of a compensator thickness profile, a target region of interest, and a dose representation on at least one of the plurality of planar reconstructions. The method also includes receiving an adjustment of at least one compensator thickness value via a manipulation of the graphical depiction thereof, and dynamically updating the at least one of the compensator thickness profile and the dose representation graphically depicted on the at least one of the plurality of planar reconstructions responsive to the received adjustment.

In accordance with another aspect, a compensator thickness visualization and modification system includes a display device, at least one user input device, and one or more processors. The one or more processors are configured to generate a series of planar slice images from a patient data set, each of the series of images having one view axis perpendicular to a direction of a radiation beam and at a user-selected viewing angle within all available perpendicular (azimuthal) viewing directions. The processors are further configured to graphically depict a compensator thickness profile, at least one isodose line, and a target of interest on one of the series of planar slice images perpendicular to the treatment beam's axis on the display device. The processors are also configured to dynamically update the compensator thickness profile and the at least one isodose line in response to the received manipulation of the graphical depiction thereof. In addition, the one or more processors are configured to automatically update a compensator thickness value table in response to the manipulation of the graphical depiction thereof.

One advantage is that a clinician is able to view simultaneously a target of interest, a compensator thickness profile, and isodose lines including depth of penetration on a single display within a single plane.

Another advantage resides in the ability of a clinician to visualize the correlation in compensator thickness and isodose levels with the target.

Another advantage resides in the efficient visualization and manipulation of the radiation dose distribution via the correlated compensator thickness profile, isodose lines, and target planar slice image.

Another advantage resides in the ability of a clinician to graphically manipulate the compensator thickness in a visualization and immediately see the resulting change in the downstream (distal) dose surface.

Another advantage resides in the capability of automatically updating a compensator thickness value table in response to adjustments made to the compensator profile displayed to the clinician.

Another advantage resides in the capability to select a cell from a compensator thickness value table and automatically view an appropriate planar slice image that includes the location on the compensator corresponding to the location associated with the cell.

Another advantage resides in the capability to select a location graphically using a tool on the currently displayed compensator thickness profile and have the software automatically navigate and display the corresponding thickness table cell showing the corresponding compensator thickness value and cell location.

Another advantage is the ability to use an analysis tool that interacts with the graphically displayed compensator thickness profile and displays the current physical properties of the compensator, including the (x, y) location, physical (z) thickness, and water equivalent thickness.

Another advantage resides in the ability to show graphically the correlation between selected rows/columns in the compensator thickness table with displayed compensator thickness profile and vice versa. As the user navigates through the perpendicular slices showing different compensator thickness profiles, the corresponding row or column of cells making up the displayed compensator profile are highlighted.

Another advantage is the ability of the software to display the anatomy, compensator thickness, and dose in a beam relative view (BRV) and to display in this additional view navigation lines. These lines depict the currently displayed perpendicular beam relative view (PBRV) plane's location within the beam relative view (BRV). These navigation lines are automatically updated as the user scrolls through the perpendicular view slices or changes their azimuthal view angle. The user may interact with the navigation lines displayed in the beam relative view and move them to new locations, or rotate these lines when they bisect the beam's central axis. The system automatically updates display of the perpendicular slices to reflect the new locations of the navigation lines.

Another advantage is the ability of the software to perform the embodiments of the invention regardless of compensator fabrication method. The method allows for visualization and thickness modification of compensators fabricated using plunge, continuous, and other fabrication methods.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

FIG. 1 schematically illustrates an embodiment of a compensator thickness visualization and modification system.

Figure 6:
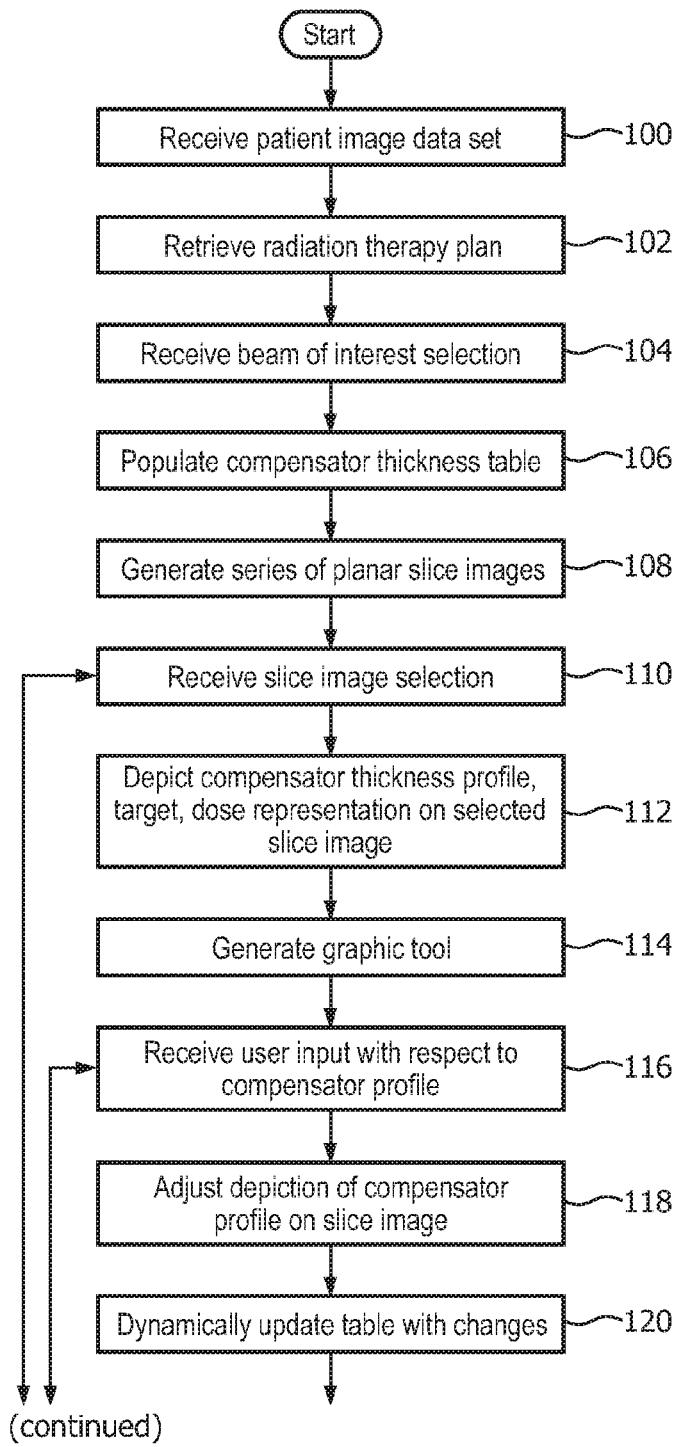
Figure 6:
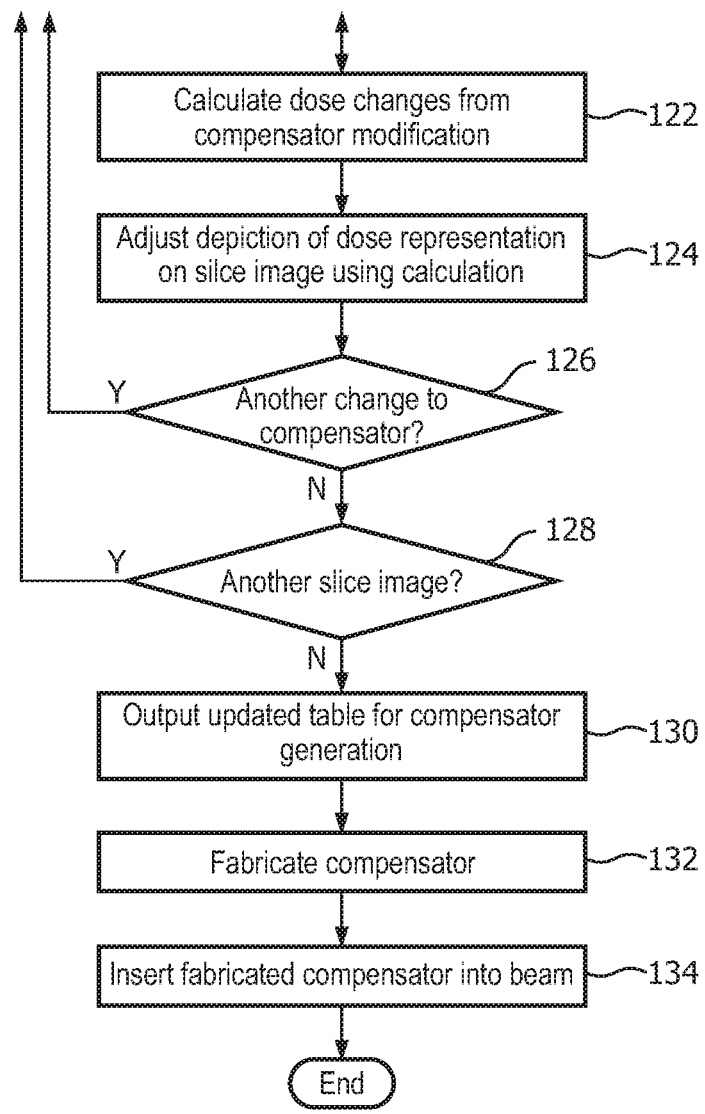

FIG. 6 flowcharts one method of compensator thickness visualization and modification.

Figure 1:
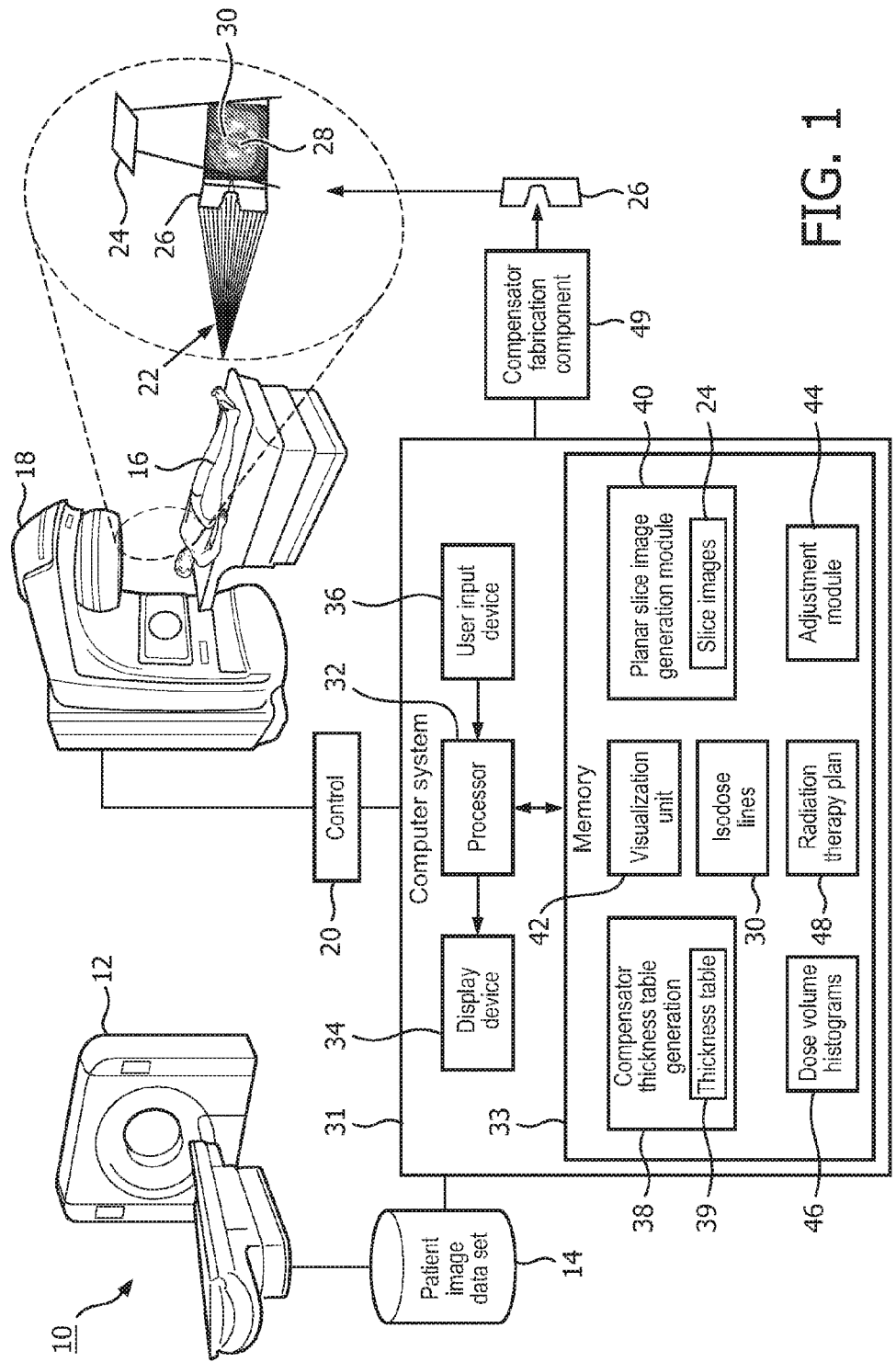

With reference to FIG. 1, an embodiment of a compensator thickness visualization and modification system 10 is schematically illustrated. The system 10 can receive patient image data 14 of a subject 16 focusing on a region of interest including a target 28. The patient image data 14 inclusive of the target 28 may be from a CT image device 12, a magnetic resonance imaging device (MRI), a PET/CT imaging device, or other suitable imaging device.

Figure 2:
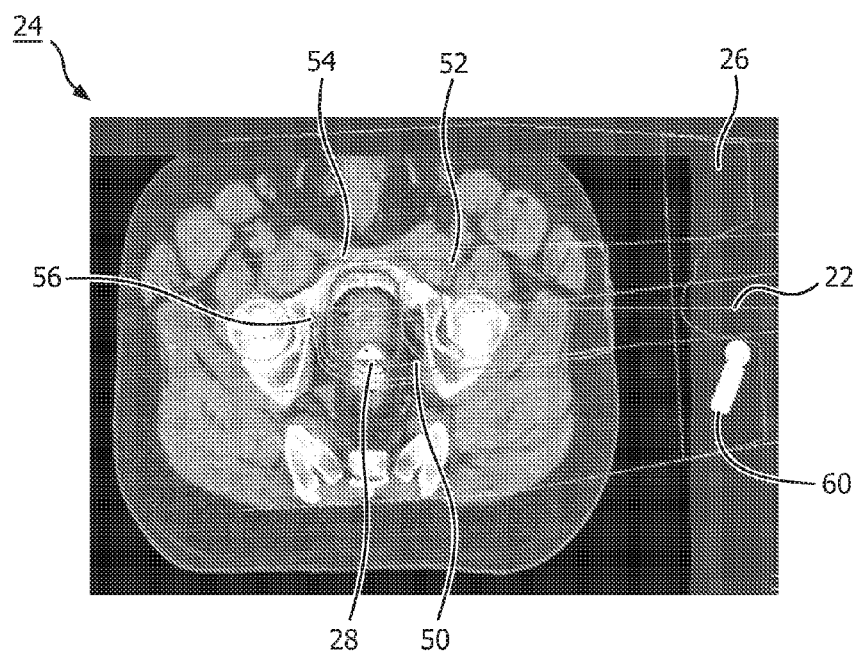
FIG. 2 illustrates a planar slice image according to one embodiment.

In one embodiment, the system 10 can receive planned isodose lines 30 and/or dose volume histograms (DVHs) 46 for the target 28 of interest of the subject 16 based upon a radiation therapy plan 48. The radiation therapy plan 48 may be based upon an IMRT approach, a VMAT approach, IMPT approach, constant intensity broad beam proton therapy, and the like, or the system 10 can construct the isodose lines 30 and/or DVHs 46 from IMRT or VMAT information such as beams or related fluence maps, IMPT beams, broadbeam proton beams, or the like. The radiation therapy plan 48 may include control instructions for a treatment delivery device 18. The treatment delivery device 18 includes a control 20 which executes the control instructions according to a radiation therapy plan to deliver radiation to the target of interest 28 of the subject 16. As will be appreciated, the treatment delivery device 18 may deliver proton or photon beams 22 in accordance with the radiation therapy plan 48 to the subject 16. The control 20 may further receive and execute instructions for controlling an upstream component of the isodose lines 30 relative to the beam of radiation 22 sent into the subject, as illustrated in FIG. 2, discussed below. The control signals control the treatment delivery device 18 in the delivery of the external beam of radiation 22. As depicted in FIG. 1, the beam 22 transits a compensator 26 having varied thickness, to control the downstream isodose lines 30, as explained in detail below.

The system 10 employs a compensator 26 to modify the depth of penetration of the beam of radiation 22 into the subject 16. The compensator 26 is a physical device disposed between the source of the beam 22 (treatment delivery device 18) and the subject 16. The compensator 26 may be comprised of various materials, dependent upon the source of radiation. For example, when used in photon therapy utilizing x-rays, a metal plate, such as brass, may be utilized and milled as the compensator 26; when used in proton therapy, a cylindrical piece of material, e.g., plexi-glass (acrylic), blue wax, or the like, can be machined to have a suitable thickness pattern to control the downstream depth of the beam 22 into the subject 16. It will be appreciated that the thickness pattern of the compensator 26 is suitably determined in accordance with the anatomy of the subject 16 and the desired depth of penetration into the subject 16, as illustrated in FIG. 2. Fabrication of the compensator 26 is discussed below with respect to the fabrication component 49.

The system 10 illustrated in FIG. 1 includes a computer system 31 that includes at least a processor 32 in communication with memory 33. The memory 33 includes processed data, such as dose volume histograms 46, radiation therapy plans 48, planar slice images 24, compensator thickness tables 39, and the like as discussed below. The memory 33 also includes one or more processor executable instructions that, when executed by the processor 32, coordinate operations of the computer system 31, as well as interfacing with the image device 12 and the treatment delivery device 18. The processor 32 executes the processor executable instructions stored in the memory 33.

The system 10 includes a compensator thickness value table module 38 configured to generate a table 39 of the various thicknesses of a compensator 26 disposed between the beam 22 and the subject 16. That is, the module 38 is capable of populating a table 39 of thicknesses of the compensator 26 at particular locations on the compensator 26. The table 39 may include rows and columns corresponding to coordinates (x,y) on the compensator 26, wherein each cell is the physical thickness of the compensator 26 at that particular location. It will be appreciated that the table 39, as updated below, may be used to generate a compensator 26 for incorporation in the radiation therapy plan 48 for the subject 16. In some embodiments, the table 39 may be used to machine, mill, mold, or otherwise form a physical compensator 26 to be disposed between the treatment delivery device 18 and the subject 16 during a subsequent course of the radiation therapy plan 48.

The system further includes a planar slice image generating module 40 configured to reconstruct a series of planar slice images 24 from the patient image data set 14. The series of planar slice images 24 may represent a series of images, spaced a predetermined distance apart, one in which the image planes lie perpendicular to the beam's central axis 22, and the in which the image planes lie parallel to the beam's central axis 22. In some instances, an arbitrary viewing angle may be selected by a clinician, such that one view axis remains perpendicular to the beam 22 while the second view axis corresponding to the slice image 24 is transverse at the arbitrarily selected viewing angle. The series of slice images 24 can be spaced any desired distance apart in the 3-D patient image data set 14 by the module 40. For example, slice images 24 may have a distance of 5 mm between them, 2 mm between them, or the like, as directed by the clinician. It will be appreciated that the distance selected between the slice images 24 may be dependent upon the size of the target 28, e.g., small tumors have rather small distances between the slice images 24, larger tumors having greater distances between the slice images 24, a shape of the target 28, a type of tumor corresponding to the target 28, and so forth. In some embodiments contemplated herein, a clinician may select a particular cell in the table 39, whereupon the planar slice image module 40 automatically retrieves or reconstructs the slice image 24 in which the location of the cell is depicted.

The system 10 includes a visualization unit 42 which visualizes planar slice images 24, isodose lines 30, the compensator 26, radiation beams 22, and the like, on an associated display device 34. The visualization unit 42 may include a graphical selection component, i.e., graphic tool 60 (shown in FIG. 2), which allows an associated clinician to graphically adjust the compensator 26 e.g., clicking and dragging the inset portion of the compensator 26 towards or away from the target 28, right or left clicking to increase or decrease the thickness at a point on the compensator 26, or the like. In one embodiment, the visualization unit 42 provides a clinician with a graphical user interface configured to receive input via a user input device 36, to graphically alter the shape of the compensator 26 displayed in a particular planar slice image 24, to display a thickness table 39 and allow modification of one or more cells in the table 39 so as to modify the thickness of the compensator 26 at the location corresponding to the cell, and the like. The visualization unit 42 may include additional tools to graphically assist the clinician in modifying a radiation therapy treatment plan 48, visualize changes to the compensator 26, adjust isodose lines 30, and the like. The visualization unit 42 can also enable a clinician, via the graphical user interface displaying the table 39, to select a cell, row, or column, in the table 39 and accordingly visualize the planar slice image 24 illustrating the compensator thickness value(s) of the cell, row, or column at the location(s) on the compensator associated with the cell, row, or column The system 10 also includes an adjustment module 44 configured to receive user input via the graphic tool 60 of the visualization unit 42 and adjust the visual display of the compensator 26 on the planar image slice 24 displayed on the display device 34 in conjunction with the visualization unit 42. The adjustment module 44 may further be configured to provide input to the table generation module 38, so as to enable the table module 38 to update the compensator thickness value table 39 in response to adjustments made to the compensator 26 via the graphic tool 60. The adjustment module 44 may further be configured to interact with the control 20 to adjust the upstream isodose line 30 with respect to the target 28 following fabrication and insertion of the compensator 26.

The system 10 further includes a compensator fabrication component 49 configured to receive compensator thickness information, e.g., the thickness table 39, and to facilitate fabrication of the compensator 26 in accordance with the values set forth in the table 39. The fabrication component 49 may be implemented as a computer-controlled milling system, which utilizes the received table 39 to mill a blank, billet, or the like, of a suitable material into the compensator 26 having the appropriate thickness values. It will be appreciated that other machining or fabrication processes may be used in producing the compensator 26 having the selected thickness values as set forth in the received table 39. The fabricated compensator 26 thus produced may then be placed in the beam 22 as the last beam line component, thereby enabling treatment of the subject 16 in accordance with the radiation therapy plan 48.

The planar slice image 24 depicted in FIG. 1 is shown in greater detail in FIG. 2, along with close-up views of the various isodose lines 30 and target 28. Turning now to FIG. 2, there is shown a single planar slice image 24 generated from the patient image data set 14 by the planar slice image generating module 40. The planar slice image 24 is generally a single voxel in width, and corresponds to a view of the target 28 in the subject 16 at a selected angle different than the commonly utilized beam's eye view referenced above. That is, the view of the planar slice image 24 corresponds to an arbitrary angle of viewing relative to the beam 22. As illustrated in FIG. 2, the view of the planar slice image 24 includes one axis that is parallel to the beam 22 and one axis that is perpendicular to the beam 22, i.e., looking down on the beam 22 so as to provide a view of the depth of the beam 22 into the subject 16 relative to the target 28, as well as a cross-sectional view of the compensator 26, enabling the visualization of the thickness of the compensator 26 with respect to this particular planar slice image 24.

As depicted in FIG. 2, the planar slice image 24 illustrates several isodose lines 50, 54, and 56 surrounding the target of interest 28 created by the beam 22 as it passes into the subject 16. As will be appreciated, the downstream edges of the isodose lines 50-56 are capable of being adjusted by the beam source (treatment delivery device 18), i.e., the depth of penetration of the beam 22 into the subject 16 is controlled via the control 20. A target 28 depicted in the planar slice image 24 illustrated in FIG. 2 is drawn by a clinician via the visualization unit 42. The target 28 is then designated and assigned to a beam, and the compensator thickness is determined by standard ray tracing methods. The compensator 26 is then rendered on the image 24 representative of an initial attempt at targeting the radiation beam 22 on the target 28. A graphical tool 60 generated via the visualization unit 42 in accordance with the adjustment module 44, enables the clinician to modify the compensator 26 thickness to achieve the desired isodose line 50 to conform more accurately to the target. It will be appreciated that by modifying the compensator 26, the depth of penetration on the downstream end of the beam 22 can be adjusted deeper or shallower in response so as to extend over or past the target 28. Conversely, by adjusting the isodose lines with the tool 60, the visualization of the compensator thickness can be adjusted.

The illustration of FIG. 2 also depicts varying isodose lines representative of various amounts of radiation to the subject 16. For example, an 80% level isodose line 52 is depicted indicating the application of 80% of the reference radiation level to all pixels through with the line passes, whereas 50% of the reference radiation level is applied to the pixels connected by the isodose line 56 and 20% to the pixels denoted by the isodose line 58. In accordance with one embodiment, a clinician is able to adjust the thickness of the compensator 26 on this planar slice image 24 by moving the graphical tool 60 in the direction desired, with the increase or decrease in coverage indicated immediately on the display. The compensator thickness value table module 38 may receive the inputs from the graphical tool 60 and the adjustment module 44 to automatically update the cell or cells in the table 39 associated with the changes made by the clinician corresponding to the new thickness values.

Figure 3:
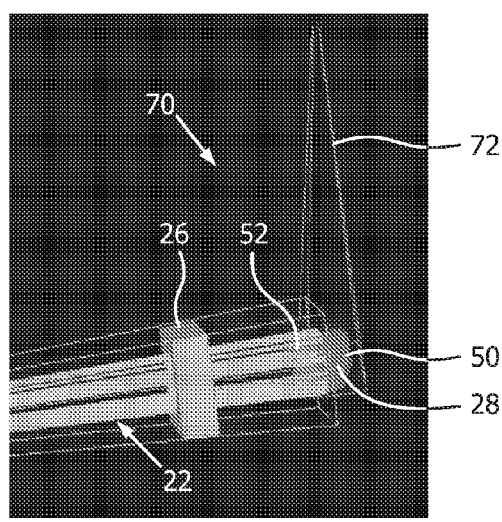
FIG. 3 illustrates a three-dimensional representation of a radiation treatment beam and a viewing beam.

FIG. 3 depicts a three-dimensional view 70 illustrating the viewpoint 70 of the slice image 24 of FIG. 2. As shown in FIG. 3, the compensator 26 is disposed between the source (not shown) and the target 28. The isodose lines 50 and 52 are illustrated as isodose surfaces around the target 28 in view 70. It will be appreciated that the direction of view shown in FIG. 2 is depicted in FIG. 3 at reference 72, illustrating that the clinician is viewing a planar slice image 24 having one view axis that is perpendicular to the direction of the beam 22 and the other view axis at an arbitrary polar angle to the direction of the beam 22. FIG. 3 is drawn to merely illustrate the isodose surfaces 50 and 52, and it will be appreciated that the beam 22 is depicted therein to show direction, and the beam 22 may stop at end of the isodose line around the target as illustrated in FIG. 2.

Figure 4:
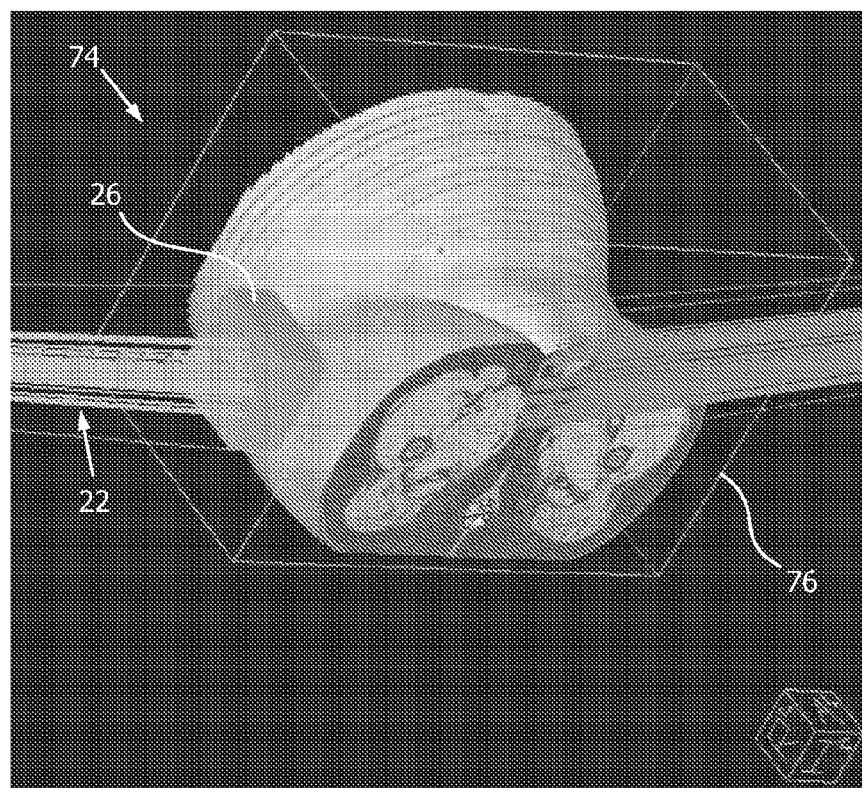
FIG. 4 illustrates a three-dimensional representation of the radiation treatment beam and a viewing beam at a user-specified azimuthal angle.

FIG. 4 depicts a three-dimensional view 74 illustrating a viewpoint 76 (shown in FIGS. 5A-5B below), at an azimuthal angle of 45 degrees off the patients anterior-posterior direction. As shown in FIG. 4, the compensator 26 is located between the source (not shown) and the target (not shown). The view 76 shown in FIG. 4 is illustrative of the clinician viewing a planar slice image 78 (e.g., FIGS. 5A-5B) having one axis that is perpendicular to the direction of the beam 22 and the other axis at the azimuthal angle of 45 degrees. The various isodose lines 52-56, target 28, etc., are further illustrated in FIGS. 5A-5B. The angle of 45 degrees is not unique, and the clinician may specify an angle between 0-360 degrees, depending on preference or need to visualize a desired anatomical structure.

Figure 5A:
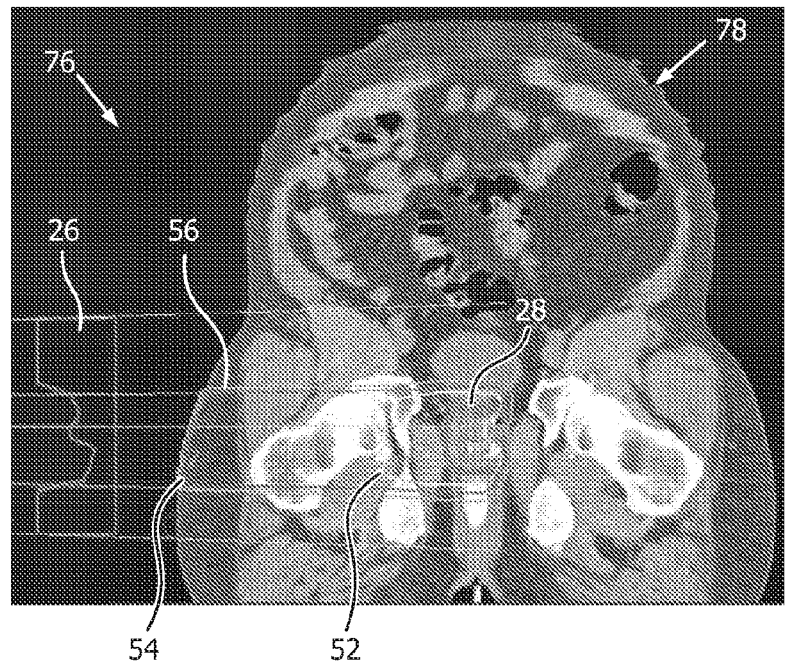
FIG. 5A illustrates a two-dimensional representation of a reconstructed slice for a perpendicular view beam depicted in FIG. 4 for a compensator whose thickness produces a dose distribution that does not fully cover the target.

FIG. 5A illustrates a two-dimensional representation of a reconstructed slice 78 for a perpendicular view beam 76 depicted in FIG. 4 for a compensator 26 whose thickness produces a dose distribution that does not fully cover the target 28. As shown in FIG. 5A, the viewpoint 76 represents a 45 degree azimuthal angle relative to the direction of the beam 22. The various isodose lines 52, 54, and 56 in FIG. 5A are shown in association with the thickness of the compensator 26. That is, the various lines 52-56 are depicted as affected by the thickness of the compensator 26 implemented in FIG. 5A.

Figure 5B:
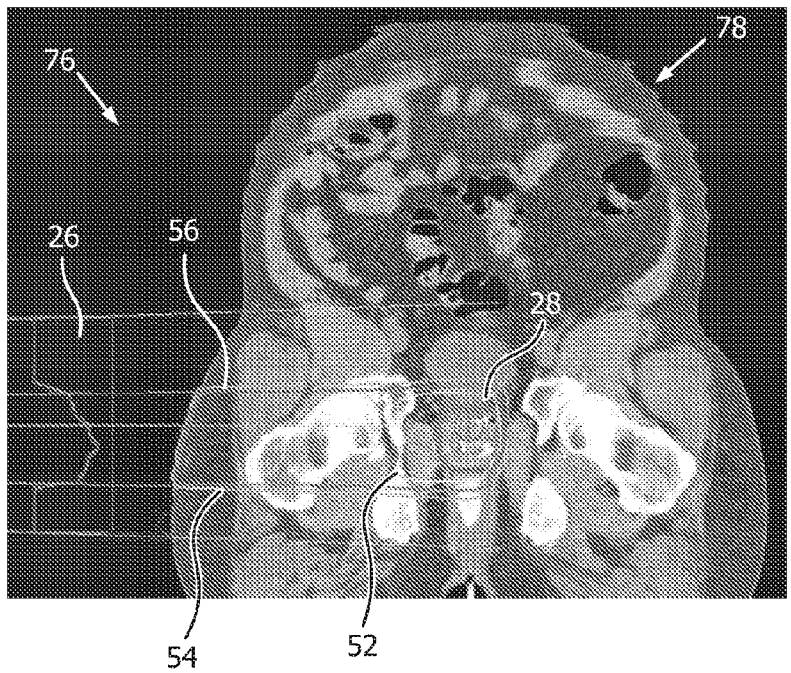
FIG. 5B illustrates a two-dimensional representation of the reconstructed slice for a perpendicular view beam of FIG. 5A where the compensator thickness has been adjusted such that the dose now follows the target in the shown slice in the perpendicular view.

FIG. 5B illustrates a two-dimensional representation of the reconstructed slice 78 for a perpendicular view beam 76 of FIG. 5A wherein the thickness of the compensator 26 has been adjusted such that the isodose lines 52, 54, and 56 more closely follow the target 28 in the shown slice 78 in the perpendicular view 78. As will be appreciated, the thickness of the compensator 26 depicted in FIG. 5A results in an under dose coverage, which is remedied by the modified compensator 26 shown in FIG. 5B. As discussed above, a clinician may adjust the thickness of the compensator 26 depicted in FIG. 5A via the graphic tool 60 to remedy the under dose shown with respect to isodose line 52, with the resulting compensator thickness value table 39 updated to reflect the new thickness of the compensator 26 shown in FIG. 5B. Once the thickness of the compensator 26 is acceptable to the clinician, as indicated by the appropriate coverage of the target 28, the updated thickness value table 39 may be output to the compensator fabrication component 49 for fabrication of the compensator 26 as discussed below.

FIG. 6 flowcharts one method of visualizing and modifying compensator thickness, which can be performed by one or more processors. In step 100, a patient image data set 14 is received from an image scanner 12, storage, or the like, corresponding to a subject 16. In one embodiment, the patient image data set 14 suitably corresponds to a region of interest on the subject, e.g., a portion of the subject's anatomy wherein a tumor, organ, etc., is located. At step 102, a radiation therapy plan 48 is retrieved from memory 31 corresponding to the subject 16. It will be appreciated that the radiation therapy plan 48 may include data relating to the subject 16, image segmentation data, beam parameter data, calculated dose data, preset isodose levels, and the like. At 104, a beam of interest is selected by the clinician for dose evaluation in accordance with the systems and methods set forth herein. It will be appreciated that when a radiation therapy plan 48 contains more than one treatment beam 22, the clinician will select the beam of interest for dose evaluation for that beam 22 and possible compensator element 26 thickness adjustment.

At step 106, a compensator thickness table 39 is populated by the compensator thickness table generation module 38 corresponding to the radiation therapy plan 48 retrieved at step 102, in response to a preset compensator 26 selected by a clinician, or the like. At step 106, a series of planar slice images 24 is generated by the planar slice image generation module 40 from the received patient image data set 14. In one embodiment, the clinician selects a desired thickness between each slice image 24 in the series thereof. That is, the clinician may select a thickness of 2 mm, 4 mm, 5 mm, or the like, in between each planar image 24 generated from the patient image data set 14. In other embodiments, the variation between planar slice images 24 may be preselected in accordance with operation of the system 10, selected in accordance with a type of tumor being treated, or the like.

At step 110, a selection of a slice image 24 for viewing on the display device 34 is selected by the clinician or automatically generated in accordance with preselected parameters. In one embodiment, the selection of the slice image 24 for viewing is made via selection of a cell in the thickness value table 39. That is, the clinician may select a value in a cell of the table 39, whereupon the visualization unit 42 or other suitable component associated with the system 31 automatically selects the appropriate slice image 24 from the series that displays the compensator profile 26 having that selected thickness value. Other embodiments may determine the selection of the slice image 24 based upon the type of target 28 being treated, location in the anatomy of the subject 16, or the like.

In accordance with one embodiment, the systems and methods discussed herein are capable of coordinated display and navigation with a corresponding beam relative view (BRV) viewer, where by the current perpendicular view plane location is depicted by a navigation line in the BRV view. In such an embodiment, by scrolling through the perpendicular view planes, e.g., slice images 24, the clinician would have the system update the position of the navigation line. Alternatively, moving the location of the navigation line will scroll through the series of perpendicular view planes, i.e., the series of planar slice images 24.

At 112, the visualization unit 42 graphically depicts the profile of the compensator 26 along a line, e.g., a row, column, or oblique line of the table 39, the target 28 of interest, dose levels (e.g., isodose lines 30), and the like, on the selected planar slice image 24 on the display device 34. A suitable example of such a graphical depiction is illustrated in FIG. 2, as discussed above. In step 114, a graphic tool 60 is generated on the planar slice image 24 via the visualization unit 42. As discussed above, the graphic tool 60 is displayed on planar image slice 24 so as to allow the clinician to adjust the thickness of the compensator 26 and/or the isodose lines 30. User input from the clinician is then received at 116 via the user input device 36 corresponding to an adjustment of a thickness of the profile of the compensator 26 graphically depicted on the planar slice image 24 displayed on the display device 34. It will be appreciated that the graphical tool 60 may be visualized on the slice image 24 in proximity to the profile of the compensator 26 and may include a family of forms for pushing or pulling, and with different radii or other shape characteristics.

At 118, the graphical depiction of the compensator 26 is dynamically adjusted in response to the adjustments made by the clinician at 116. In one embodiment, the adjustment module 44 is configured to receive the user input and modify/adjust the display of the compensator 26 on the planar slice image 24.

At 120, the compensator thickness table generation module 38 updates the table 39 corresponding to the radiation therapy plan 48 in response to the modifications made with the graphic tool 60. The generation module 38 may automatically, i.e., dynamically, update one or more cells in the table 39 to reflect the corresponding change(s) in thickness to the locations on the compensator 26 associated with the cell(s).

At 122, the changes to the isodose lines 30 are calculated in accordance with the modification(s) made to the compensator 26. The adjustment module 44 then facilitates, at 124, the adjustment of the depiction of the dosage, i.e., isodose lines 30 on the slice image 24 in accordance with the calculations of 122. That is, the changes made by the clinician to the compensator 26 and/or updated table 39 affect the downstream locations of the isodose lines 30, as illustrated in the correlating images in FIG. 2. In some embodiments, algorithms are utilized by the processor 32 to calculate the adjustments to the isodose lines 30 in response to the user made modifications to the compensator 26. The visualization unit 42 may facilitate the graphical display of the adjusted compensator 26 and isodose lines 30, as shown in FIG. 2. In accordance with one embodiment, the clinician may utilize the graphic tool 60 to move isodose lines 30 to new locations relative to the target 28, particular organs, particular tissues, etc. In such an embodiment, the systems and methods set forth herein enable the automatic calculation of compensator thickness values for the compensator 26 to effectuate those changes. Accordingly, the table 39 would then be suitably updated to reflect the calculated thickness values resulting from the clinician's movement of the isodose lines 30 via the graphic tool 60.

At 126, a determination is made whether another change has been made by the clinician. That is, a determination is made whether the clinician has utilized the graphic tool 60 to further modify the compensator 26 or isodose lines 30. Upon a positive determination, operations return to step 116, whereupon user input with respect to the profile of the compensator 26 depicted on the planar slice image 24 is received and proceed thereafter as set forth above. Upon a determination that no further changes are to be made to the compensator 26, operations progress to 128, whereupon a determination is made whether the clinician wishes to view another planar slice image 24 from the series generated from the patient image data set 14. Upon a positive determination, operations return to step 110, whereupon the next slice image 24 is selected and operations proceed as set forth above. Upon a negative determination at 128, the updated table 39 is output to the compensator fabrication component 49 for generation (e.g., fabrication, modification, milling, etc.,) of the compensator 26 to be used in the radiation therapy plan 48 on the subject 16 at step 130.

The compensator 26 corresponding to the updated table 39 is then fabricated at step 132 via the compensator fabrication component 49. At step 134, the fabricated compensator 26 is inserted into the beam 22 so as to deliver the radiation therapy plan 48 to the subject 16. It will be appreciated that the fabrication and installation of the compensator 26 may be during a subsequent series of treatments of the subject 16. It will further be appreciated that during the treatment of the subject 16, additional compensators 26 may need to be designed and fabricated in accordance with the systems and methods set forth herein in response to changes in the target 28, e.g., the tumor has shrunk or enlarged, etc.

Thus, the systems and methods set forth herein provide a clinician with a visualization of isodose lines 30, a cross-sectional view of the compensator 26, and the target 28. The graphical tool 60 provided on the visualization allows the clinician to adjust the thickness of the compensator 26, which automatically updates the isodose lines 30 displayed, allowing the clinician to adjust the depth of penetration of the beam 22, deeper or shallower, depending upon the target 28 (size, shape, position, etc.) and the radiation therapy plan 48 associated with the subject 16. Each of the series of slice images may be viewed, allowing the clinician to adjust the thickness of the compensator 26 for each plane. Once all planes are acceptable, a compensator thickness value table 39, having cells that correspond to locations and corresponding thickness values, is updated and output for the creation of the physical compensator 26 or adjustment/machining to be made to the compensator 26 for completion of the radiation therapy plan 48.

As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), an FPGA, and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a LCD display, an LED display, a plasma display, a projection display, a touch screen display, a CRT display, and the like.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. A compensator thickness visualization and modification system, comprising:
   a planar slice image generation module for generating a series of planar slice images from a patient image data set disposed with one view axis parallel to a radiation beam and one view axis perpendicular to the radiation beam;
   a visualization unit for graphically depicting at least one of a compensator thickness profile, a target of interest, and a dose representation on at least one of the series of planar slice images, wherein the dose representation comprises a visualization of a radiation dose pattern and a visualization of a depth of penetration of radiation; and
   an adjustment module for receiving user input of an adjustment of at least one of the compensator thickness profile and the dose representation via a manipulation of the graphical depiction thereof,
   wherein the visualization unit is configured to dynamically update the dose representation including adjustment of the visualization of the radiation dose pattern and the visualization of the depth of penetration of radiation.

2. The system according to claim 1, further comprising:
   a compensator thickness table generation module for automatically updating a compensator thickness table associated with the compensator thickness profile responsive to the received user input.

3. The system according to claim 2, wherein:
   the visualization unit is configured to receive user input corresponding to a selection of at least one cell in the compensator thickness table and generate one of the series of planar slice images on an associated display device corresponding to a depiction of a compensator at a location thereon associated with the at least one selected cell.

4. The system according to claim 2, wherein the visualization unit is configured to dynamically update the at least one of the compensator thickness profile and the dose representation graphically depicted on the at least one of the series of planar slice images in response to the user input received via the adjustment module.

5. The system according to claim 2, wherein the adjustment module is further configured to provide input to the compensator thickness table generation module for updating the compensator thickness table.

6. The system according to claim 1, wherein the visualization unit is configured to receive user selection input of a viewing angle, wherein the planar slice image generation module generates the series of planar slice images disposed with one axis perpendicular to the radiation beam and the other axis at the viewing angle relative to the radiation beam.

7. The system according to claim 1, wherein the dose representation comprises at least one isodose line adjacent to the target of interest.

8. The system according to claim 1, wherein each image in the series of planar slice images has a preselected thickness.

9. The system according to claim 8, wherein the preselected thickness of each planar slice image is selected in accordance with at least one of a user input, a size of the target of interest, and a shape of the target of interest.

10. A method for visualizing and modifying compensator thickness, comprising:

generating, from a patient image data set, a series of planar slice images disposed with one view axis parallel to a radiation beam and one view axis perpendicular to the radiation beam;

graphically depicting at least one of a compensator thickness profile, a target of interest, and a dose representation on at least one of the series of planar slice images, wherein the dose representation comprises a visualization of a radiation dose pattern and a visualization of a depth of penetration of radiation;

receiving an adjustment of at least one of the compensator thickness profile and the dose representation via a manipulation of the graphical depiction thereof; and dynamically updating the at least one of the compensator thickness profile and the dose representation graphically, including the visualization of the radiation dose pattern and the visualization of the depth of penetration of radiation, depicted on the at least one of the series of planar slice images responsive to the received adjustment.

11. The method according to claim 10, wherein the dose representation comprises at least one isodose line adjacent the target of interest.

12. The method according to claim 10, further comprising:

automatically updating a compensator thickness value table in response to the received adjustment via the manipulation of the graphical depiction.

13. The method according to claim 12, wherein the automatic updating of the compensator thickness value table includes modifying a value in at least one cell of the table corresponding to the manipulation of the graphical depiction of the at least one compensator thickness value.

14. The method according to claim 12, further comprising:

receiving user input corresponding to a selection of at least one cell in the compensator thickness value table;

identifying one of the series of planar slice images corresponding to a depiction of a compensator at a location associated with the at least one selected cell; and generating a visualization of the identified one of the series of planar slice images on an associated display device.

15. The method according to claim 14, further comprising:

generating a graphic tool on the identified one of the series of planar slice images, wherein receiving the adjustment includes receiving a manipulation of the graphic tool.

16. The method according to claim 10, further comprising:

receiving user selection input of a viewing angle, wherein generating the series of planar slice images further comprises generating the series of planar slice images disposed with one axis perpendicular to the radiation beam and the other axis at the viewing angle relative to the radiation beam.

17. A non-transitory computer-readable storage medium carrying software which controls one or more electronic data processing devices to perform the method according to claim 10.

18. A compensator thickness visualization and modification system, comprising:

a display device;

at least one user input device; and one or more processors configured to:

generate a series of planar slice images from a patient data set, each of the series of images having one axis perpendicular to a propagation direction of a radiation beam and one at a selected viewing angle within all available perpendicular viewing directions;

graphically depict a compensator thickness profile, at least one isodose line, and a target of interest on one of the series of planar slice images on the display device;

dynamically update the compensator thickness profile and the at least one isodose line in response to a received manipulation of the graphical depiction thereof; and automatically update a compensator thickness value table in response to the received manipulation of the graphical depiction thereof.

* * * * *